US00PP13016P2

(12) United States Plant Patent
Lamb et al.

(10) Patent No.: US PP13,016 P2
(45) Date of Patent: Sep. 24, 2002

(54) SPATHIPHYLLUM PLANT NAMED 'MARIA'

(75) Inventors: Ann Elizabeth Lamb, Sebring; David R. Lilly, Boynton Beach, both of FL (US)

(73) Assignee: Twyford International Inc., Santa Paula, CA (US)

( * ) Notice: Subject to any disclaimer, the term of this patent is extended or adjusted under 35 U.S.C. 154(b) by 2 days.

(21) Appl. No.: 09/846,436

(22) Filed: May 2, 2001

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Annette H. Para
(74) *Attorney, Agent, or Firm*—C. A. Whealy

(57) ABSTRACT

A distinct cultivar of Spathiphyllum plant named 'Maria', characterized by its upright, somewhat outwardly arching and symmetrical plant habit; large and broad glossy dark green leaves with slightly undulate leaf margins and thick petioles; rapid growth rate; and large pure white spathes that are positioned well above the foliage on strong, thick and erect peduncles.

2 Drawing Sheets

BOTANICAL CLASSIFICATION

Spathiphyllum hybrid cultivar Maria.

BACKGROUND OF THE INVENTION

The present Invention relates to a new and distinct cultivar of Spathiphyllum plant, botanically known as Spathiphyllum hybrid, and hereinafter referred to by the cultivar name Maria.

The new cultivar is a product of a planned and controlled breeding program conducted by the Inventors in Apopka, Fla. The objective of the breeding program is to create Spathiphyllum cultivars with improved plant habit, dark green foliage and rapid growth rate. The new cultivar originated from a deliberate cross made by the Inventors in March, 1997 of a unnamed selection of Spathiphyllum, not patented, as the female or seed parent and the Spathiphyllum cultivar Jetty, disclosed in U.S. Plant Pat. No. 9,957, as the male or pollen parent. The cultivar Maria was discovered and selected by the Inventors as a plant within the progeny of the stated cross in a controlled environment in Apopka, Fla., on Oct. 28, 1998.

Asexual propagation of the new cultivar by tissue culture since October, 1998, in a laboratory in Sebring, Fla., has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity, fertilizer level and propagation procedures, without, however, any variance in genotype.

The following traits have been repeatedly observed and are determined to be the unique characteristics of 'Maria'. These characteristics in combination distinguish 'Maria' as a new and distinct cultivar:

1. Upright, somewhat outwardly arching and symmetrical plant habit.

2. Large and broad glossy dark green leaves with slightly undulate leaf margins and thick petioles.

3. Rapid growth rate.

4. Large pure white spathes that are positioned well above the foliage on strong, thick and erect peduncles.

Plants of the new Spathiphyllum differ from plants of the female parent, the unnamed selection of Spathiphyllum hybrid, when grown in side-by-side comparisons in Sebring, Fla., in the following characteristics:

1. Plants of the new Spathiphyllum are smaller than plants of the female selection.

2. Plants of the new Spathiphyllum have broader and more rugose leaves than plants of the female selection.

3. Leaf margins of plants of the new Spathiphyllum are more undulate than leaf margins of plants of the female selection.

Plants of the new Spathiphyllum differ from plants of the male parent, the cultivar Jetty, when grown in side-by-side comparisons in Sebring, Fla., in the following characteristics:

1. Plants of the new Spathiphyllum are more upright and not as outwardly spreading than plants of the cultivar Jetty.

2. Plants of the new Spathiphyllum have darker green and glossier leaves than plants of the cultivar Jetty.

3. Leaf margins of plants of the new Spathiphyllum are not as undulate than leaf margins of plants of the cultivar Jetty.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Spathiphyllum.

The photograph at the top of on the first sheet comprises a side perspective view of a typical 7.5-month old plant of 'Maria' grown in a 15-cm container.

The photograph at the bottom of the first sheet comprises a side perspective view of typical plants of 'Jetty', left, and 'Maria', right.

The photograph at the top of the second sheet comprises a top perspective view of typical plants of 'Maria', left, and 'Jetty', right, showing the differences in leaf color.

The photograph at the bottom of the second sheet comprises a side perspective view of typical plants of 'Jetty', left, and 'Maria', right, showing the differences in plant shape.

DETAILED BOTANICAL DESCRIPTION

The following observations, measurements and comparisons describe 7.5-month old plants (from planting rooted tissue-cultured plantlets) grown during the winter and spring in Homestead, Fla., in a polypropylene-covered shadehouse and under commercial production conditions in 15-cm containers. During the production of the plants, day temperatures ranged from 70 to 90° F., night temperatures ranged from 65 to 75° F., and light levels were about 1,500 foot-candles.

In the following description, color references are made to The Royal Horticultural Society Colour Chart except where general terms of ordinary dictionary significance are used.

Botanical classification: Spathiphyllum hybrid cultivar Maria.

Parentage:

*Female parent.*—Unnamed selection of Spathiphyllum hybrid, not patented.

*Male parent.*—Spathiphyllum hybrid cultivar Jetty, disclosed in U.S. Plant Pat. No. 9,957.

Propagation:

*Type.*—By tissue culture.

*Time to initiate roots on a tissue-cultured cutting.*—Summer: About 6 to 8 days at 70 to 90° F., day temperature, and 65 to 75° F., night temperature. Winter: About 7 to 10 days at 70 to 90° F., day temperature, and 65 to 75° F., night temperature.

*Time to produce a fully-rooted tissue-cultured plantlet.*—Summer: About 70 days at 70 to 90° F., day temperature, and 65 to 75° F., night temperature. Winter: About 84 days at 70 to 90° F., day temperature, and 65 to 75° F., night temperature.

*Root description.*—Thick, white, fleshy; lateral branch roots, fine.

*Rooting habit.*—Freely branching.

Plant description:

*Plant shape.*—Upright, somewhat outwardly arching and symmetrical plant habit; intermediate in stature.

*Growth habit.*—Erect when young, becoming somewhat outwardly arching as leaves develop. Freely clumping and full appearance. Plants of the new Spathiphyllum are typically grown in 15 to 20-cm containers.

*Plant height.*—About 55 cm from soil level to top of leaf plane.

*Plant spread.*—About 68 cm.

*Growth rate.*—Rapid growth rate; from tissue-cultured plantlets, about 6.5 to 7 months are required to produce finished flowering plants in 15-cm containers and about 8 to 9 months are required to produce finished flowering plants in 20-cm containers.

*Foliage description.*—Length: About 32 cm. Width: About 17 cm. Shape: Broadly ovate. Apex: Elongated acuminate. Base: Obtuse. Margin: Entire, slightly undulate. Aspect: Initially upright, then somewhat outwardly arching; slightly reflexed at apex. Surface: Rugose; midrib and lateral veins, sunken on upper surface and prominent on lower surface. Texture, both surfaces: Leathery, smooth, glabrous, durable and flexible. Color: Young, upper surface: Initially 146A then close to 147A, glossy. Young, lower surface: Close to 147B, dull. Mature, upper surface: Darker than 147A, glossy. Mature, lower surface: Close to 147B, dull. Petiole: Aspect: Initially erect, outer leaves about 40 to 45° from vertical with development; outwardly bent at geniculum. Length: About 30.5 cm. Diameter, base: About 1.2 cm. Diameter, just below geniculum: About 6 mm. Diameter, just above geniculum: About 5.5 mm. Wing length: About 24 cm. Wing width: About 1.1 cm. Geniculum length: About 3.75 cm. Geniculum diameter: About 7.5 mm. Strength: Strong and thick, but flexible. Color: Petiole and wings: 147A. Geniculum: Darker than 146A to close to 147A.

Inflorescence description:

*Inflorescence arrangement/quantity.*—Concave spathes with spadices held well above the foliage on strong and erect peduncles. Freely flowering; typically about three developing and open spathes per plant at one time; inflorescences arise from leaf axils.

*Time to flower.*—Plants of the new Spathiphyllum flower continuously and year-round under greenhouse production conditions.

*Inflorescence longevity.*—Spathes generally maintain white color for about four weeks on the plant. As cut flowers, spathes maintain good substance for about seven days.

*Fragrance.*—Slightly fragrant, sweet, typical of Spathiphyllum.

*Spathe.*—Length: About 15 cm. Width: About 9.5 cm. Shape: Elliptic. Apex: Elongated acuminate. Base: Obtuse. Aspect: Concave, curling over the spadix. Color, both surfaces: White, closest to 155D, becoming green, close to 144A, with development. Back surface midvein, between 144A to 146A.

*Spadix.*—Length: About 11.2 cm. Diameter, midsection: About 2 cm. Color: 158B to 158D becoming green, closest to 143A, with development. Quantity of flowers: More than 300 per spadix. Pollen: Abundant, white, close to 155D.

*Peduncle.*—Aspect: Very strong and thick. Length: Base of peduncle to base of spathe: About 53 cm. Base of spathe to stipe: About 2.5 cm. Stipe: About 5 mm. Diameter, at base of spathe: About 8 mm. Diameter, at base of peduncle: About 7 mm. Color: Close to 146A; towards base, close to 145C.

*Seed.*—Seed development has not been observed.

Disease/pest resistance: Plants of the new Spathiphyllum have not been observed to be resistant to pathogens or pests common to Spathiphyllum.

Temperature tolerance: Plants of the new Spathiphyllum have been observed to tolerate temperatures from 45 to 104° F.

It is claimed:

1. A new and distinct cultivar of Spathiphyllum plant named 'Maria', as illustrated and described.

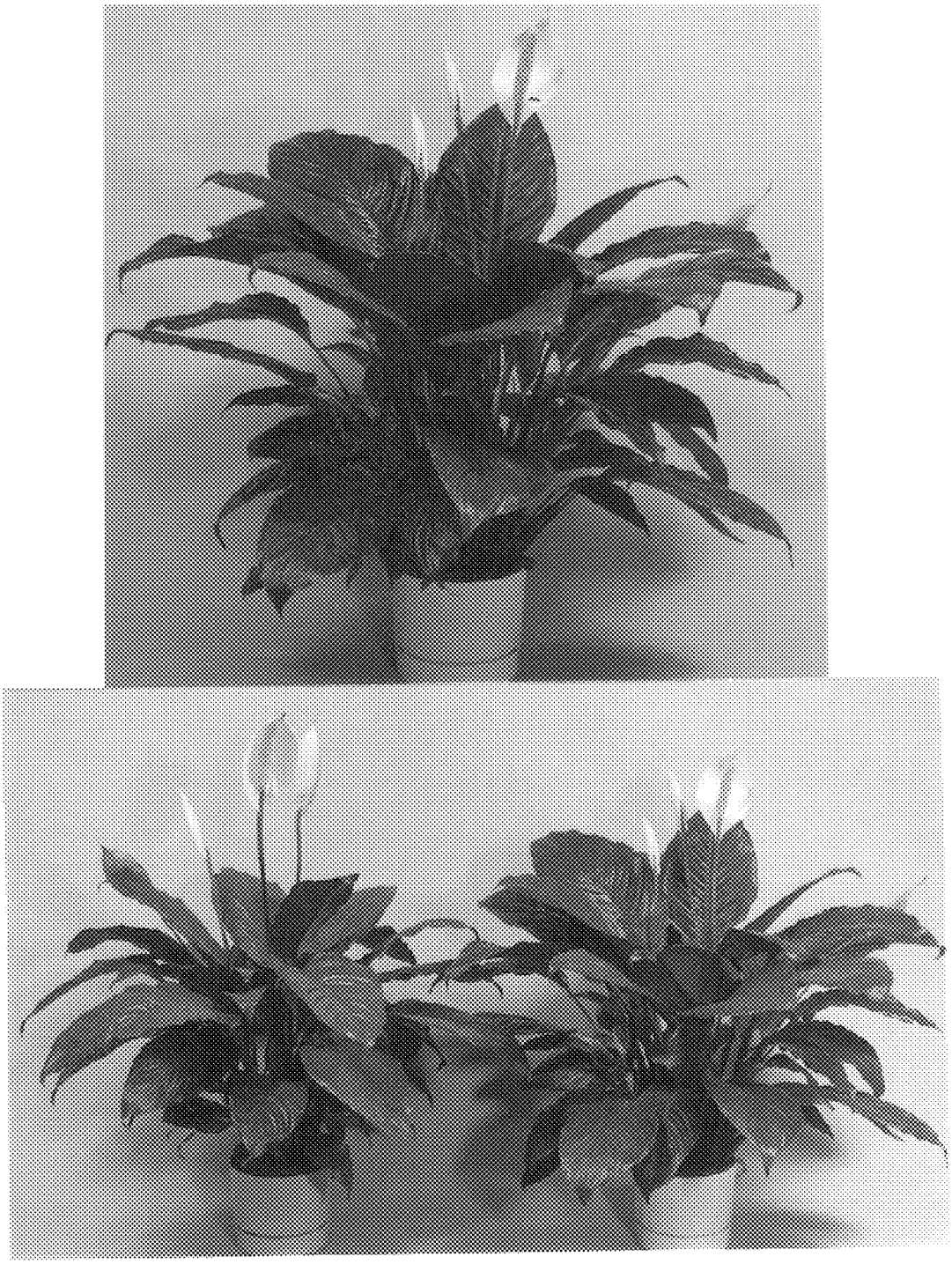

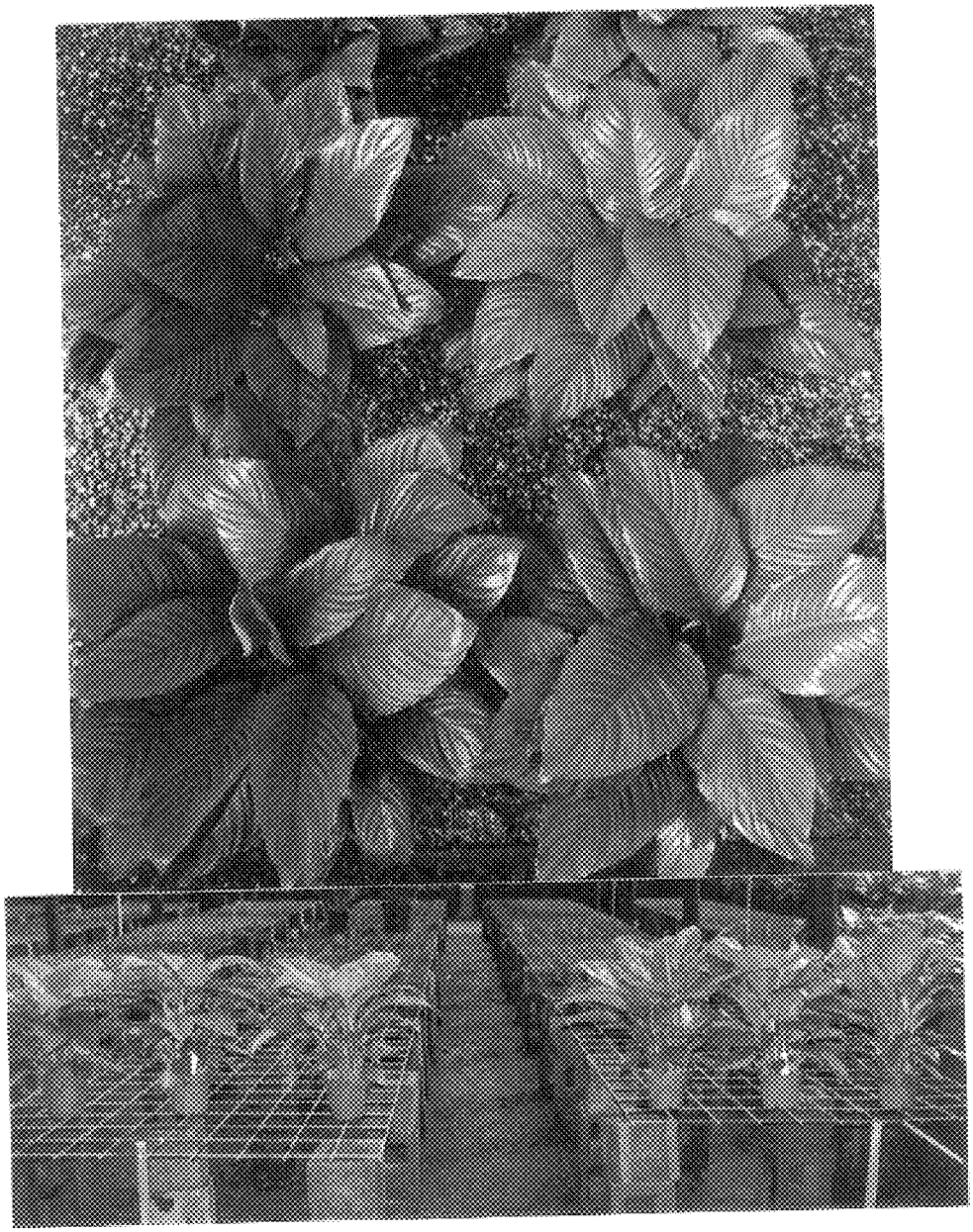

* * * * *